United States Patent [19]

Lemp et al.

[11] Patent Number: 5,425,741
[45] Date of Patent: Jun. 20, 1995

[54] TISSUE CUTTING DIE

[75] Inventors: Steven K. Lemp, Santa Barbara; Philip J. Hudak, Burbank; Charles S. Love, Newbury Park, all of Calif.

[73] Assignee: Autogenics, Newbury Park, Calif.

[21] Appl. No.: 169,620

[22] Filed: Dec. 17, 1993

[51] Int. Cl.⁶ .................................. A61B 17/32
[52] U.S. Cl. ..................................... 606/167
[58] Field of Search ............... 606/167, 184, 166, 131, 606/132; 128/750-758, 858; 30/301, 316, 358; 83/531, 541; 623/2

[56] References Cited

U.S. PATENT DOCUMENTS

| | | |
|---|---|---|
| 2,822,819 | 2/1958 | Geeraert . |
| 2,922,437 | 1/1960 | Rippingille . |
| 3,026,823 | 3/1962 | Wilcox . |
| 3,532,016 | 10/1970 | Lane . |
| 3,548,418 | 12/1970 | Angell et al. . |
| 3,570,014 | 3/1971 | Hancock . |
| 3,613,242 | 10/1971 | Hill et al. ................ 606/132 |
| 3,714,671 | 1/1973 | Edwards et al. . |
| 3,755,823 | 9/1973 | Hancock . |
| 3,967,645 | 7/1976 | Gregory . |
| 3,983,581 | 10/1976 | Angell et al. . |
| 4,011,947 | 3/1977 | Sawyer . |
| 4,035,849 | 7/1977 | Angell et al. . |
| 4,065,816 | 1/1978 | Sawyer . |
| 4,084,268 | 4/1978 | Ionescu et al. . |
| 4,101,031 | 7/1978 | Cromie . |
| 4,172,295 | 10/1979 | Batten . |
| 4,182,446 | 1/1980 | Penny . |
| 4,192,020 | 3/1980 | Davis et al. . |
| 4,211,241 | 7/1980 | Kaster et al. . |
| 4,247,292 | 1/1981 | Angell . |
| 4,297,749 | 11/1981 | Davis et al. . |
| 4,388,735 | 6/1983 | Ionescu et al. . |
| 4,470,157 | 9/1984 | Love . |
| 4,490,859 | 1/1985 | Black et al. . |
| 4,501,030 | 2/1985 | Lane . |
| 4,512,471 | 4/1985 | Kaster et al. . |
| 4,535,819 | 8/1985 | Atkinson et al. . |
| 4,597,767 | 7/1986 | Lenkei . |
| 4,605,407 | 8/1986 | Black et al. . |
| 4,643,732 | 2/1987 | Pietsch et al. . |
| 4,679,556 | 7/1987 | Lubock et al. . |
| 4,687,483 | 8/1987 | Fisher et al. . |
| 4,692,164 | 9/1987 | Dzemeshkevich et al. . |
| 4,725,274 | 2/1988 | Lane et al. . |
| 4,801,015 | 1/1989 | Lubock et al. . |
| 4,838,288 | 6/1989 | Wright et al. . |
| 4,865,033 | 9/1989 | Krumeich et al. ............... 606/166 |
| 4,881,562 | 11/1989 | Wright et al. . |
| 5,037,434 | 8/1991 | Lane . |
| 5,147,391 | 9/1992 | Lane . |
| 5,163,955 | 11/1992 | Love et al. ..................... 623/2 |

FOREIGN PATENT DOCUMENTS

| | | |
|---|---|---|
| 5796865 | 10/1966 | Australia . |
| 1243453 | 10/1988 | Canada . |
| 0051451 | 5/1982 | European Pat. Off. . |
| 0116236 | 8/1984 | European Pat. Off. . |
| 0179562 | 4/1986 | European Pat. Off. . |
| 2391708 | 12/1978 | France . |
| 1189399 | 4/1970 | United Kingdom . |
| 1264472 | 2/1972 | United Kingdom . |
| 1598112 | 2/1978 | United Kingdom . |
| 2046165 | 11/1980 | United Kingdom . |
| 2169386 | 1/1986 | United Kingdom . |
| 9115167 | 10/1991 | WIPO . |

OTHER PUBLICATIONS

Barratt-Boyes, "A Method for Preparing and Inserting a Homograft Aortic Valve", Brt. J. Surg, Nov. 1965, vol. 52, No. II, pp. 847-856.

(List continued on next page.)

*Primary Examiner*—Stephen C. Pellegrino
*Assistant Examiner*—William W. Lewis
*Attorney, Agent, or Firm*—Knobbe, Martens, Olson & Bear

[57] ABSTRACT

The present invention provides a novel tissue cutting device for autologous tissue heart valves which accurately cuts the tissue to a predetermined configuration in a minimal amount of time. The disposable tissue cutting die of the present invention is comprised of a cover, a base member, a continuous blade enclosing a desired spatial configuration and an actuator for forcing said tissue against the entire perimeter of the blade.

26 Claims, 6 Drawing Sheets

OTHER PUBLICATIONS

Reis, et al., "The flexible stent: A new concept in the fabrication of tissue heart valve prostheses", The Journal of Thoracic and Cardiovascular Surgery, Nov. 1971, vol. 62, No. 5, pp. 683–689; 693–695.

Yates, "A fascial frustum valve for aortic valve-replacement", Thorax 1971, vol. 26, pp. 184–189.

Brownlee, et al., "A fascia lata mitral valve based on the 'frustum' Principle", Thorax, 1971, vol. 26, pp. 284–287.

Bartek, et al., "Frame-mounted tissue heart valves: technique of construction", Thoraz, 1974, vol. 29, pp. 51–55.

Ionescu, et al., "Replacement of heart valves with frame-mounted tissue grafts", Thorax, 1974, vol. 29, pp. 56–67.

Black, et al., "A construction technique for minimizing valve leaflet fatigue failure in pericardial valves", Life Support Systems, Proceedings XI Annual Meeting ESAO, Alpbach-Innsbruck, Austria, Sep. 1984, vol. 2, Supp. 1.

Love, et al., "Degenerative calcification in tissue valves a metabolic/hemodynamic or immunologic problem", Abstract published for the International Associate for the Cardiac Biological Implants, Chicago, Apr. 5, 1987, p. 1.

Love, et al., "Experimental Evaluation of an Autogenous Tissue Heart Valve", Poster Presentation at the IV International Symposium Cardiac Bioprostheses, San Diego, Apr. 15, 1988.

Reul, et al., "In Vitro Testing of Bioprostheses", Trans. Am. Soc. Artif. Intern. Organs, 1988, vol. XXXIV, pp. 1033–1039.

Love, et al., "The Autogenous Tissue Heart Valve: Experience with Pericardium", Pericardial Tissue as a Cardiac Valve Substitute, Proceedings of a Symposium, Thumberbach, Austria, Sep. 1988, pp. 31–40.

Khan, et al., "Doppler and Hemodynamic Characteristics of the Autogenics Bioprosthetic Valve", p. 1.

TISSUE CUTTING DIE

FIELD OF THE INVENTION

This invention relates to cutting devices and is particularly directed to tissue cutting dies used to precisely and accurately cut various tissues to a particular predetermined configuration, particularly in the fashioning of an autologous tissue heart valve.

BACKGROUND OF THE INVENTION

Heart valves are typically replaced due to birth defects, stenosis (narrowing) of the valve (in which case the heart must exert a great deal of force to pump the blood through the valve) or insufficiency or incompetence of the valve, whereby the heart is unable to prevent backflow of the blood. The diseased or damaged heart valve is removed from the patient and replaced with some type of artificial or prosthetic valve.

The three main types of prosthetic heart valves are mechanical, biological and homograft. A detailed description and background of these three types of prosthetic heart valves may be found in U.S. Pat. No. 5,163,955, assigned to Autogenics, assignee of the present application and incorporated herein by reference. These valves, however, have proven to be costly and present an increased risk to the patient with respect to durability and acceptability.

Most recently, autologous tissue valves, i.e. valves constructed with the patient's own tissue, have been investigated. However, since this type of valve utilizes the patient's own tissue, the valve must usually be assembled during the same surgical procedure in which the patient's diseased or damaged valve is removed. Therefore, valve assembly must be completed in a rapid and efficient manner to avoid further risk to the patient.

To construct an autologous heart valve, one typically fits or mounts the patient's tissue onto a stent or some other type of valve frame. This can be accomplished by several methods. In one conventional method, the individual valve leaflets are cut from a roughly sized piece of tissue and individually sewn or attached onto the frame. In another method, a single piece of roughly sized tissue is attached to the valve frame and the excess tissue is trimmed away. Both of these methods, however, have proven to be time-consuming and unreliable.

The above referenced '955 patent discloses a novel and substantially improved cutting die for quickly and precisely cutting autologous tissue into the desired configuration. This die, however, does not provide the major improvements and advantages which have been incorporated into the cutting die of the present invention. These advantages will become apparent from the Detailed Description of the Invention, considered together with the drawings and claims.

SUMMARY OF THE INVENTION

The present invention provides a new tissue cutting device for autologous tissue heart valves which is a modification of the die disclosed in the '955 patent. The preferred embodiment of the tissue cutting die of the present invention comprises a cover, a base member, a slide or actuator, and wing nuts.

The cover is comprised of a top member which is generally rectangular in shape. Four separate blades fit within and slightly extend above the top surface of the top member. The blades are arranged in the top member so that they form a precise outline of the desired cut piece of tissue. In addition, the ends of two of the blades abut against the remaining two blades, so that there are no gaps between the blades. This advantageously ensures that the entire piece of tissue is cut in one step, including the four corners where the blades meet. Thus, no additional manual cutting steps are required to separate the two pieces of tissue.

The base member, similar to the cover, is comprised of a base piece which is generally rectangular in shape, with a tunnel running down its center length. Another component of the tissue cutting die is the slide or actuator. At the first end of the slide there is a raised portion or "bump". The second end of the slide is flat and, therefore, does not have a bump. The height of the bump is slightly greater than the height of the tunnel in the base member.

The tissue cutting die of the present invention is used in the following manner. First, a roughly sized piece of tissue is laid flat across the top surface of the base member. Next, the top surface of the cover is positioned onto the top surface of the base member and the tissue. The cover and the base member are aligned and secured together, thereby slightly embedding the blades into the piece of tissue.

The actual cutting of the tissue occurs as the slide is pulled through the tunnel of the base member. The second end of the slide not having the bump is pushed through one end of the tunnel until the second end of the slide emerges out the other end of the tunnel. Next, the user of the tissue cutting die pulls the second end of the slide until the first end of the slide is pulled along the entire length of the tunnel and emerges from the other end of the tunnel. During this procedure, the bump, located on the first end of the slide, pushes against the thin, flexible sheet. This, in turn, causes the tissue to be pushed against the blades of the cover. Thus, a uniform and consistent cutting force, independent of the force applied by the operator, is applied to the tissue so that the tissue is completely and automatically cut along the perimeter of the desired configuration of cut tissue.

After the tissue is cut, the cover is removed from the base member. Finally, the resultant, pre-configured cut piece of tissue is mounted onto the heart valve stent.

BRIEF DESCRIPTION OF THE DRAWINGS

FIG. 1a is an enlarged partial view of the tissue cutting die illustrated in FIG. 1 at a—a.

DETAILED DESCRIPTION OF THE INVENTION

Figure 1:
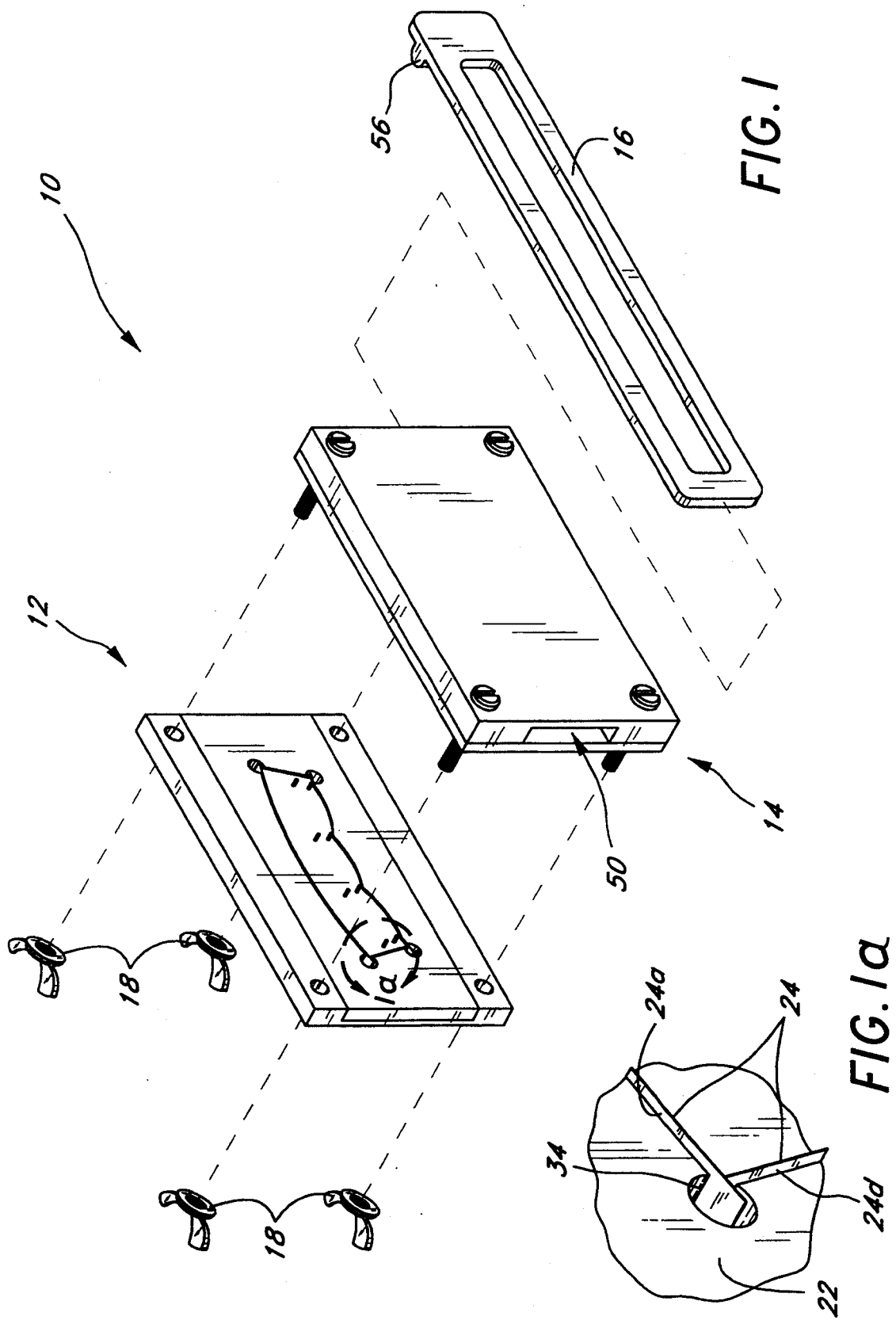
FIG. 1 is an exploded perspective view of the tissue cutting die of the present invention.

FIG. 1 illustrates an exploded view of the disposable tissue cutting die 10 of the present invention for precisely and accurately cutting tissue to a predetermined configuration for use in a medical prosthetic device such as an autologous heart valve. As discussed in detail below, the tissue to be precisely cut is placed onto the base member 14 and contacts the cutting blade 24 supported by the cover 12 when the tissue is locked between the cover 12 and the base member 14. The slide 16 is then translated through a tunnel 50 of the base member 14 to force the tissue between ridge 56 of slide 16 and the cutting blade 24 so as to precisely cut the tissue to conform to the space defined by the cutting blade 24.

Figure 2:
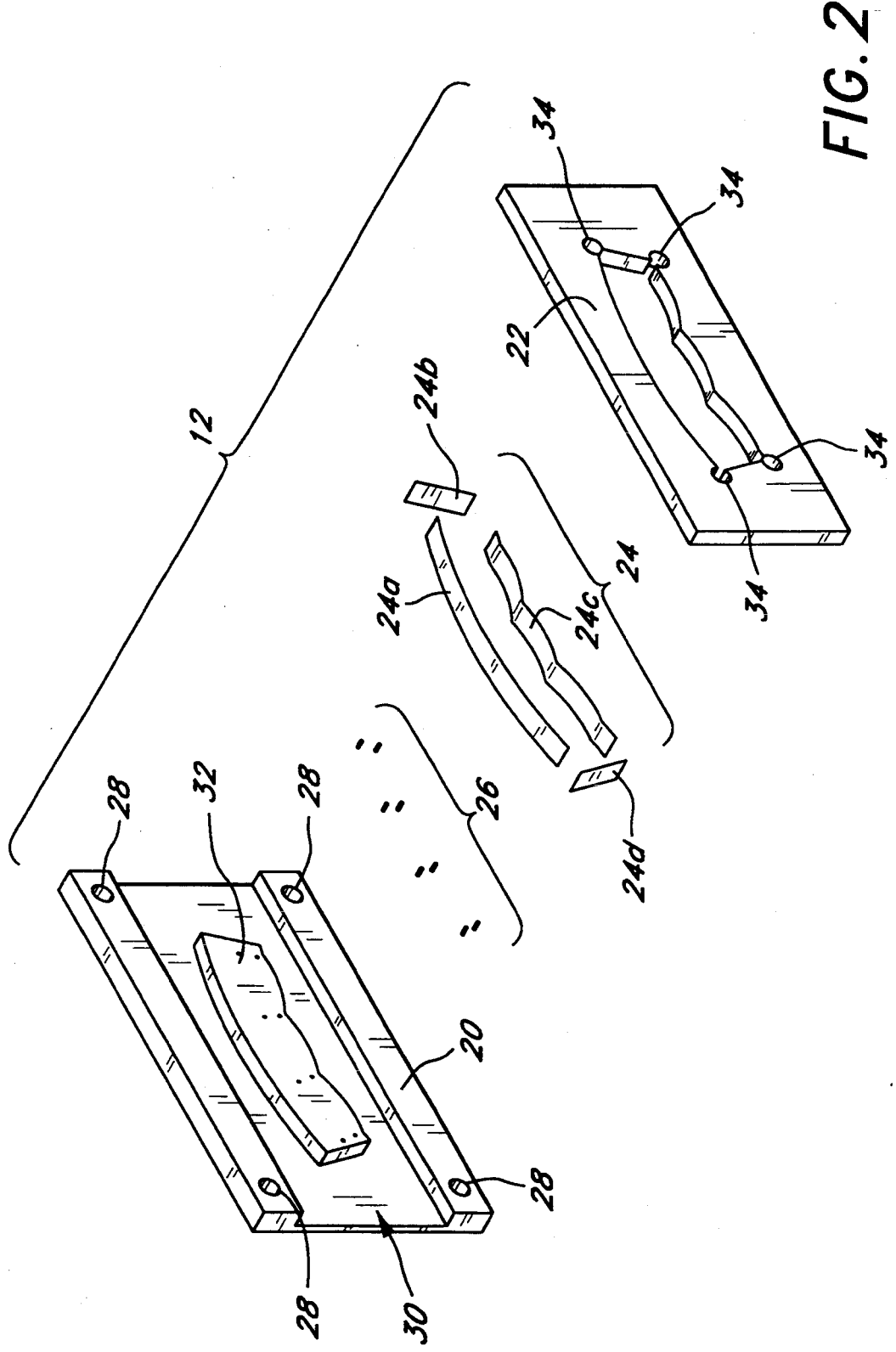
FIG. 2 is an exploded perspective view of the cover of the tissue cutting die of FIG. 1.

Referring to FIG. 2, the cover 12 includes top member 20, insert 22, cutting blade 24 and four pairs of ferrules 26. In the preferred embodiment, the top member 20 is made of a translucent polycarbonate material, preferably of biomedical grade. This top member 20 is generally rectangular in shape and has four through holes 28 located at the four corners of the top member 20. The holes are used to align and attach the cover 12 to the base member 14.

A channel 30 runs the length of top member 20 and projects into the channel 30 to form an island 32 in the middle of the top member 20. The outer periphery this island 32 is an outline of the desired cut tissue piece.

The preferred embodiment of the heart valve disclosed and claimed in the '955 patent provides an inner stent having tissue alignment members. Accordingly, the preferred embodiment of this invention includes four pairs of ferrules 26 embedded within the polycarbonate material of the island 32, the location of these ferrules 26 corresponding to the location of the tissue alignment members of the heart valve inner stent. Ferrules 26 typically extend approximately 35 mils above the top surface of the island 32. In addition, the diameter of the ferrules 26 corresponds to the diameter of the tissue alignment members.

Cover 12 further includes an insert 22, made of semi-translucent polycarbonate material, constructed so as to fit within the channel 30 and completely surround the island 32 of the top member 20. The gap between the edges of the island 32 and the insert 22 is large enough so as to accommodate and retain the cutting blade 24. In one embodiment, the insert 22 is precisely configured so that a gap of 0.002 inch or less exists between the edges of the insert 22 and the top member 20. In addition, the insert 22 has four through holes 34 located at the corresponding locations of the four corners of the island 32.

Cutting blade 24 is fixedly retained within the narrow gap between the island 32 and the insert 22. Cutting blade 24 is advantageously formed from four discrete blades 24a, 24b, 24c, 24d. These blades are advantageously formed from thin case hardened corrosion resistant steel having sufficient flexibility to conform to the shape of the gap located between the island 32 and the insert 22. The blade thickness should, however, be sufficient to prevent deflection of the blade and, consequently, an inadequately cut piece of tissue. In the preferred embodiment, the blades 24a–24d were made from a strip of 0.006 inch thick stainless steel, supplied by American Safety Razor of West Virginia, having a razor-sharpened edge. That razor-sharpened edge extends 35 mils above the top surfaces of the island 32 and the insert 22.

A significant feature of the invention is that the four corners of the space defined by the island 32 and the cutout portion of insert 22 are relieved by four through holes 34 in the insert 22. As shown in FIG. 1 and 1a, the end of the blade 24a extends into a through hole 34 with the adjoining blade 24d abutted up against. Without this relief of this cutout portion, the precise juncture of the two blades 24a, 24d would involve such tight tolerances that manufacturing practices typically dictate a slight gap between the blades. Dies constructed with gaps between adjoining blades leave a small segment of uncut tissue at the corners of the opening, requiring a manual cut after opening of the die to separate the two pieces of tissue. In contrast, the present invention merely involves making each blade 24a–24d slightly longer than the actual perimeter of the island 32, with the excess blade 24a extending into one of the holes 34.

Figure 3:
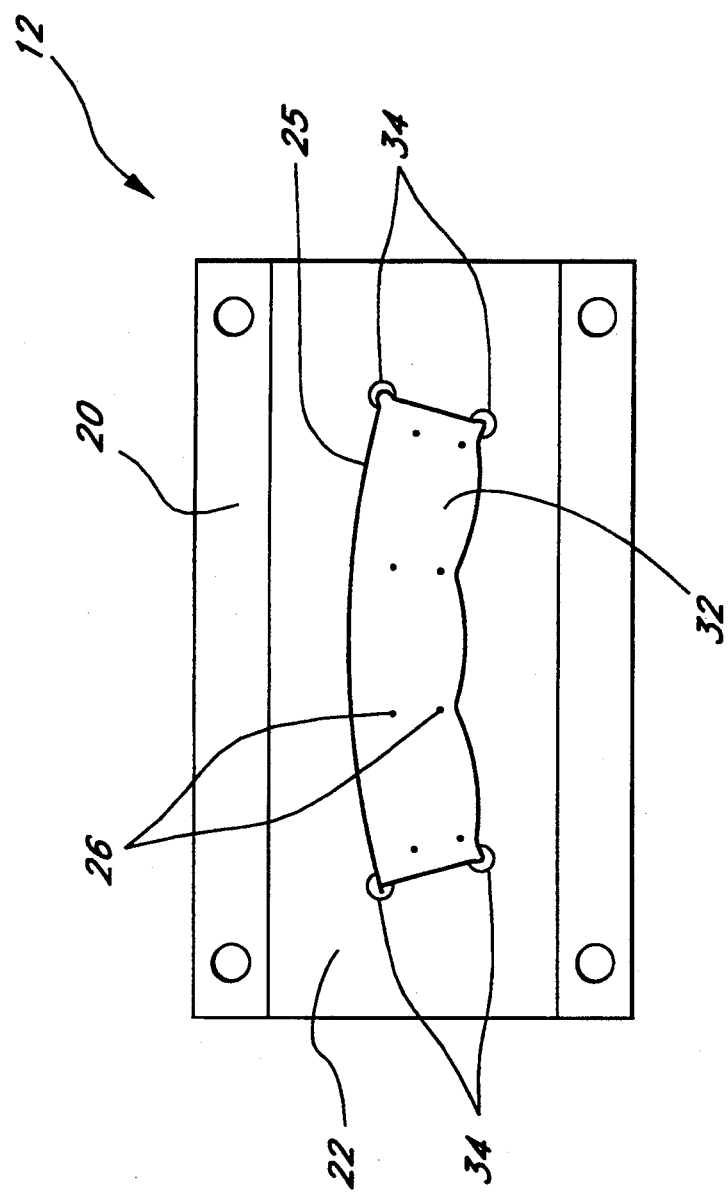
FIG. 3 is a front view of an alternate embodiment of the cover of the tissue cutting die with a one piece blade.

In an alternate embodiment of the present invention, a flexible, one piece blade 25 is used to precisely cut the piece of tissue. As shown in FIG. 3, the four through holes 34 in the insert 22 provide an additional advantage in that they allow the cover 12 to accommodate a flexible one piece blade 25. Thus, the relief provided by the radius of the through holes 34 allows a single continuous blade 25 to bend around each of the four corners of the island 32. Without the relief provided by these through holes 34, the otherwise close tolerances at the corners of the island 32 would make it difficult to accommodate a one piece blade 25. Thus, with the relief, a one piece blade 25 would have to be precisely bent to the angle formed at each of the four corners of the island 32 and still fit within the narrow gap between the island 32 and the insert 22. Therefore, the through holes 34 provide substantial additional space to allow the one piece blade 25 to bend around each of the four corners of the island 32.

Figure 4:
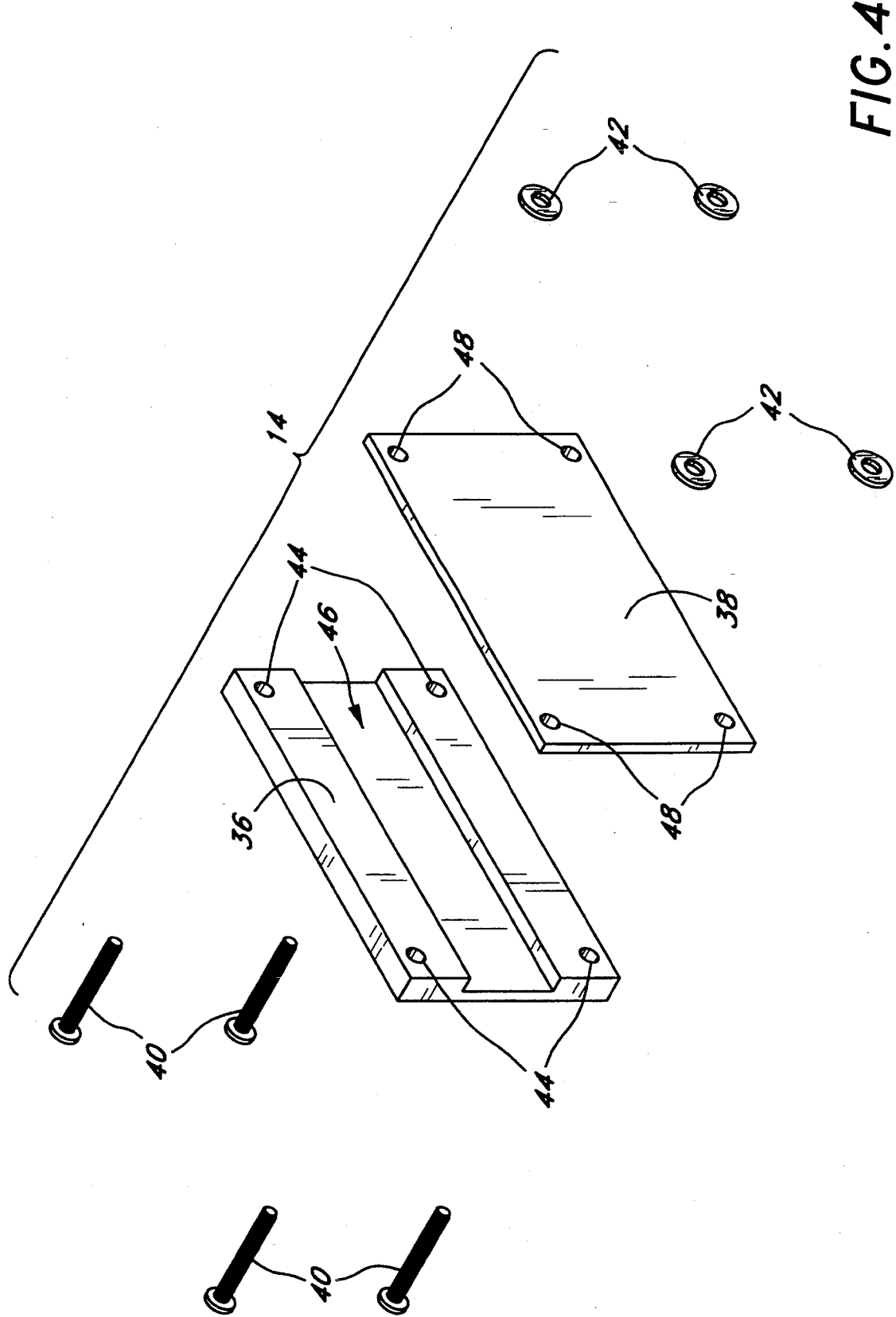
FIG. 4 is an exploded perspective view of the base member of the tissue cutting die of FIG. 1.

FIG. 4 shows an exploded perspective view of the base member 14 of the tissue cutting die 10 of the present invention, including a base piece 36, a thin flexible sheet 38, four threaded screws 40 and four washers 42. The base piece 36 of the base member 14 is advantageously made of a translucent polycarbonate material, preferably biomedical grade. The base piece 36 is generally rectangular in shape and has four threaded through holes 44 located at the four corners of the base piece 36.

A channel 46 is provided along the center length of the base piece 36 of the base member 14. The width of the channel 46 in the base piece 36 of the base member 14 accommodate the width of the island 32 and, therefore, is slightly wider than the width of the island 32.

The thin flexible sheet 38 of the base member 14 provides the cutting pad of the tissue cutting die 10. This thin flexible sheet 38 is generally 0.032 inch thick or less. TEFLON is the preferred material for sheet 38 due to its smooth surface characteristic which provides the correct amount of adhesion for the tissue. The thin flexible sheet 38 is generally rectangular in shape and is similar in size (i.e. length and width) to the top member 20 of the cover 12 and the base piece 36 of the base member 14. Located at the four corners of the thin flexible sheet 38 are four through holes 48. The location of the through holes 48 in the thin flexible sheet 38 corresponds to the location of the through holes 44 in the base piece 36 of the base member 14.

Four threaded screws 40, as shown in FIG. 4, are used to attach the thin flexible sheet 38 to the surface of the base piece 36 of the base member 14. Each screw 40 enters through the bottom surface of the base piece 36 of the base member 14 and extends through the top surface of the thin flexible sheet 38. Due to the channel 46 provided along the center length of the base piece 36 of the base member 14, the thin flexible sheet 38 creates a tunnel 50 in the base member 14, as shown in FIG. 1.

A washer 42 is positioned onto each of the screws 40 and rests on the surface of the thin flexible sheet 38. The thickness of the washers 42 is determined by the height by which the blades 24a–24d extend above the surfaces of the island 32 and the insert 22. Thus, by way of specific example, if the blades 24a–24d extend 35 mils above the surfaces of the island 32 and the insert 22, then the washers 42 must be at least 35 mils in thickness. This is to ensure that the blades 24a–24d are not damaged by the thin flexible sheet 38 during shipment of the assembled tissue cutting die 10. In addition, the washers enable the blades 24a–24d to securely hold the piece of tissue between the cover 12 and the base member 14, without actually cutting the tissue. In this specific example, the maximum thickness of the washers 42 is calculated by adding the blade height (35 mils) and half of the nominal average tissue thickness (15–20 mils).

Figure 5:
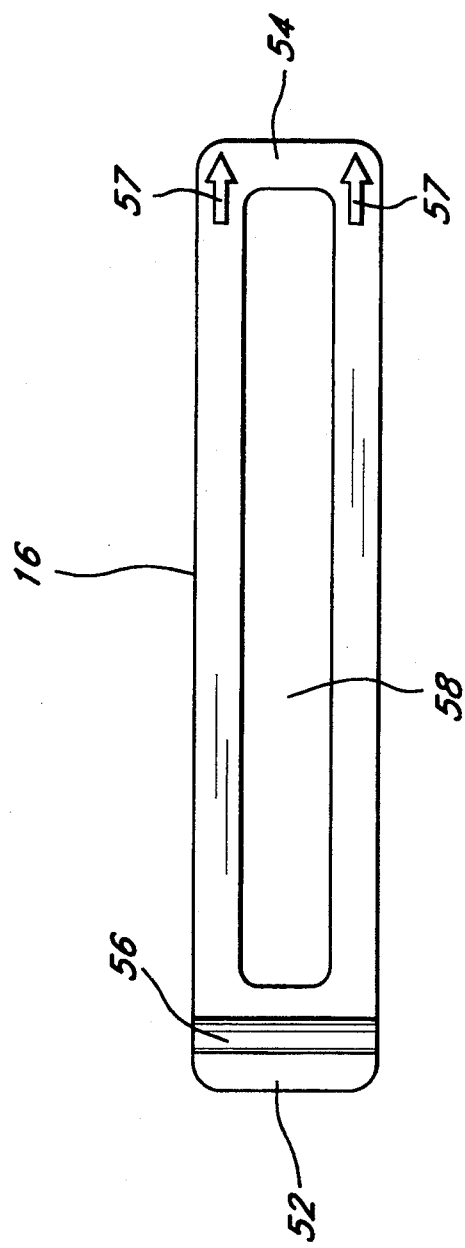
FIG. 5 is a top view of the slide of the tissue cutting die of FIG. 1.

FIG. 5 shows one embodiment of the slide 16 of the tissue cutting die 10 of the present invention. The slide 16 is longer in length but slightly narrower in width than the channel 46 in the base piece 36 of the base member 14. The slide 16 is advantageously made of thermoplastic and is similar in thickness to that of the thin flexible sheet 38. A "bump" 56 or raised portion is located on the top surface of the slide 16 near the end 52. The height of the bump 56 is equal to or slightly greater than the height of the tunnel 50 in the base member 14. The opposite end 54 of the slide 16 is generally flat. In the embodiment shown, slightly raised "arrow" symbols 57 are located on the top surface of the slide 16 near its end 54. The middle or cut-out portion 58 of the slide 16 is cut out, in the embodiment shown, so that the user's finger can be inserted within the cut-out portion proximate to arrows 57 to obtain a firmer grasp of the slide 16, and thereby facilitate the pulling of the slide 16. The use of the slide 16 will be described in detail below.

Figure 6:
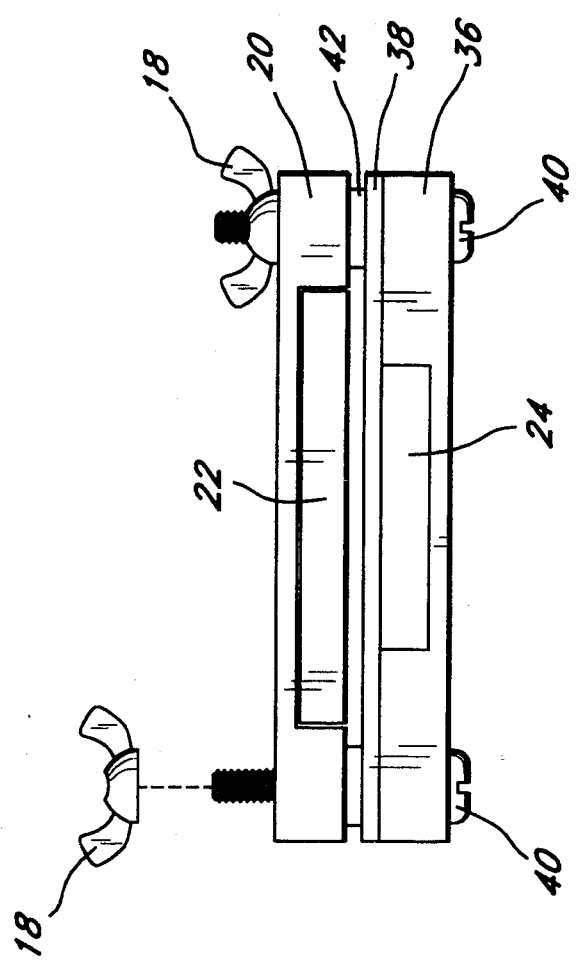
FIG. 6 is a side view of the partially assembled tissue cutting die of FIG. 1, with one wing nut screwed onto a threaded screw.

FIG. 6 illustrates a side view of the partially assembled tissue cutting die 10 of the present invention, with one of the four wing nuts 18 screwed onto one of the threaded screws 40. The wing nuts 18 are advantageously made of thermoplastic material and have a preformed internal thread. The wing nuts 18 are primarily used as a clamping means and, therefore, are of adequate size to allow one to easily and smoothly secure the wing nuts 18 onto the screws 40.

The tissue cutting die 10 of the present invention is used in the following manner. First, a roughly sized piece of tissue is laid flat across the top surface of the thin flexible sheet 38 of the base member 14. Due to the slipperiness of the patient's tissue and the adhesion characteristics of a material such as TEFLON, the tissue can be easily smoothed to lie flat across the thin flexible sheet 38. Next, the cover 12 is assembled onto the base member 14 so that the blades 24a–24d can contact the thin flexible sheet 38. This is accomplished by aligning the holes 28 located in the four corners of the cover 12 with the threaded ends of the screws 40 protruding out the top surface of the base member 14. In addition, the cover 12 and tissue are aligned so that the blades 24a–24d will cut the desired portion of the tissue.

Once the cover 12 is assembled onto the base member 14, the tissue is clamped between the two assemblies 12, 14 with the wing nuts 18. During this step, the blades 24a–24d may become slightly embedded into the tissue. However, due to the strength or toughness of the tissue, the blades 24a–24d normally do not completely penetrate the tissue.

The actual cutting of the tissue is accomplished by pulling the slide 16 through the entire length of the tunnel 50 of the base member 14. The second end 54 of the slide is pushed through one end of the tunnel 50 until it emerges out the opposite end of the tunnel 50. Due to the symmetry of the cover 12 and base member 14, the slide 16 may be pulled through either end of the tunnel 50, in the direction indicated by the "arrow" symbols 57 located on the second end 54 of the slide 16. The user of the tissue cutting die 10 pulls the second end 54 of the slide 16 until the first end 52 of the slide 16 is pulled along the entire length of the tunnel 50 and emerges out the other end of the tunnel 50. During this procedure, the bump 56, located on the first end 52 of the slide 16, pushes against the bottom surface of the thin flexible sheet 38. This, in turn, forces the tissue to be pushed against the blades 24a–24d and the ferrules 26 of the cover 12.

The bump 56 located on the first end 52 of the slide 16 produces a "wave" in the tissue and the thin flexible sheet 38. This "wave" allows one to sequentially push portions of the tissue into the blades 24a–24d, thereby enabling the blades 24a–24d to work in shear. Due to the angle between the four blades 24a–24d and the bump 56, all the blades 24a–24d are able to cut the tissue in shear.

After the tissue is cut, the wing nuts 18 are unscrewed from the threaded screws 40 so that the cover 12 may be carefully removed from the base member 14. The resultant, pre-configured cut piece of tissue is removed from the base member 14 and mounted onto the valve stent. The remaining excess tissue may be discarded.

Obviously, numerous variations and modifications can be made without departing from the spirit of the present invention. Therefore, it should be clearly understood that the forms of the present invention described above and shown in the FIGURES of the accompanying drawings are illustrative only and are not intended to limit the scope of the present invention.

What is claimed is:

1. An apparatus for cutting tissue to be used in a heart valve, said heart valve having an inner stent configured with a plurality of posts, each of said posts including outwardly-projecting tissue alignment members, and an outer stent having a plurality of posts and an expandable base with tensioning means, said inner stem positioned inside said outer stent, said outer stem tensioning means providing a clamping force securing said inner stent, said apparatus comprising:

a cover including a top member having a center length, said top member provided with a channel along said center length, said top member further including a raised island in said channel, said island having a shape corresponding to the spatial configuration into which the tissue will be cut, said island including a plurality of raised ferrules positioned to cut holes into the tissue in locations corresponding to said tissue alignment members on said inner stent, and an insert fitting within said channel, said insert containing a cutout for receiving said island, said insert completely surrounding said island and creating a narrow gap between said insert and said island when said insert is inserted into said top member, said top members and said island having a generally planar surface;

a blade with a razor sharpened edge positioned into said gap between said insert and said island, said blade edge extending above the generally planar surface of said top members and said island;

a base member removably securable to said cover during operation of said apparatus and including a base piece having a center length parallel to said center length of said cover when said base and said cover are secured together and top and bottom surfaces, said base piece having a channel along said center length, said base piece further including a flexible sheet secured to the top surface of said base piece by a plurality of securing members, the union of said base piece and said flexible sheet creating a tunnel therebetween;

an actuator member slidably mounted in said tunnel, said actuator having first and second ends, a raised portion formed near said first end and a flat region formed near said second end, said raised portion forcing a proximal portion of said flexible sheet against the top of said blade as said actuator member is translated through said tunnel so that tissue retained between said blade and said flexible sheet is automatically cut through when said actuator member is translated through said tunnel; and a plurality of attachments removably secured to said cover and said base and provided to secure said cover and said base member together.

2. The apparatus of claim 1 wherein said insert of said cover further comprises:

a plurality of holes formed at the corners of said cutout for receiving said island, said blade extending into said holes to allow the outline of said cut tissue to be continuous when said tissue is cut.

3. The apparatus of claim 1 wherein said top member is made of a translucent polycarbonate material.

4. The apparatus of claim 1 wherein said insert is made of a semi-translucent polycarbonate material.

5. The apparatus of claim 1 wherein said island and said insert form a gap of 0.002 inch or less.

6. The apparatus of claim 1 wherein said blade is rectangular in shape and flexible.

7. The apparatus of claim 1 wherein said blade is made of a high quality corrosion resistant material, such as stainless steel, with a razor sharpened edge.

8. The apparatus of claim 1 wherein said blade is 0.006 inch thick.

9. The apparatus of claim 1 wherein said blade extends 35 mils above said generally planar surface of said top members and said island.

10. The apparatus of claim 1 wherein said blade is comprised of four separate blades.

11. The apparatus of claim 1 wherein said ferrules extend 35 mils above the generally planar surface of said island.

12. The apparatus of claim 1 wherein said base piece of said base member is made of a translucent polycarbonate material.

13. The apparatus of claim 1 wherein said flexible sheet is made of TEFLON.

14. The apparatus of claim 1 wherein said slide is made of thermoplastic material.

15. The apparatus of claim 1 wherein said attachments are wing nuts.

16. An apparatus for quickly and precisely cutting a piece of autologous, homologous or heterologous tissue to a desired spatial configuration, said apparatus applying a consistent cutting force substantially independent of the force applied by the operator so that the tissue is substantially completely and automatically cut through along the perimeter of said desired spatial configuration, said apparatus comprising:

a cover having a generally planar surface;

a blade defining the perimeter of the desired spatial configuration, said blade retained in said cover and extending above the generally planar surface of said cover a length approximately equal to the thickness of the tissue to be cut;

a base member underlying and removably attachable to said cover;

a slide member slidably retained by said base member for applying a force against the entire perimeter of said blade as said slide is translated with respect to said base member along the perimeter of said blade so that a piece of tissue laid between said blade of said cover and said base member will be precisely cut substantially along the entire perimeter of said blade.

17. An apparatus for quickly and precisely cutting a piece of autologous, homologous or heterologous tissue to a desired spatial configuration, said apparatus applying a consistent cutting force substantially independent of the force applied by the operator so that the tissue is substantially completely cut through along the perimeter of said desired spatial configuration, said apparatus comprising:

a base member;

a cover member juxtaposed with said base member so that said tissue is retained between said base member and said cover member;

a blade defining the perimeter of the desired spatial configuration, said blade supported by said cover member; and an actuator member slidably mounted with respect to said base member and said cover member, said actuator member sequentially forcing segments of said retained tissue against said blade as said actuating member is moved with respect to said base and cover members so that said piece of tissue is cut through by shearing along the entire perimeter of said blade.

18. An apparatus for cutting tissue, comprising:

a cover having a top member with a center length and a channel having a raised island portion, said channel and island disposed along said center length, said cover further including an insert having a plurality of corners and a cutout conforming to said island, and a plurality of blades disposed between said insert and said island, at least a portion of said blades projecting above said island;

a base member having a base piece with a center length and a channel disposed along said center length, said base member including a flexible sheet secured to said base piece, said base piece and said flexible sheet forming a tunnel when secured together;

a slide slidably mounted in said base member and having first and second ends and a raised portion on said first end; and a plurality of attachments removably affixed to said cover and said base and provided to secure said cover and said base member together.

19. The apparatus of claim 18 wherein said insert of said cover further comprises:

a plurality of holes formed at the corners of said cutout for receiving said island, said blades extending into said holes to allow the outline of said tissue to be continuous when said tissue is cut.

20. The apparatus of claim 18 wherein said attachments are wing nuts.

21. An apparatus for cutting tissue, comprising:
a cover having a top member with a center length and a channel having a raised island portion disposed along said center length, said cover further including an insert having a cutout conforming to said island and a plurality of corners and a one piece blade disposed between said insert and said island, wherein a plurality of holes is formed at the corners of said cutout for receiving said island to allow said blade to bend around the corners of said island to allow the outline of said tissue to be continuous when said tissue is cut;
a base member removable securable to said cover and having a base piece with a center length and a channel disposed along said center length, said base piece further comprising a flexible sheet secured to said base piece, said base piece and said flexible sheet forming a tunnel;
a slide having first and second ends and a raised portion on said first end; and
a plurality of attachments removably affixed to said base and cover and provided to secure said cover and said base member together.

22. A method for precisely, repeatably cutting a piece of tissue into a predetermined shape comprising the steps of:
providing a roughly sized piece of tissue;
providing a tissue cutting die having a cover having raised blades for cutting said piece of tissue and a base member having a flexible sheet with top and bottom surfaces, said flexible sheet forming a tunnel in said base member;
laying said roughly sized piece of tissue flat across said top surface of said flexible sheet;
assembling said cover and base member of said tissue cutting die together and securing said cover and base member to each other;
providing a slide having a first end portion including a raised portion and a flat second end portion;
inserting said second end portion of said slide into said tunnel formed by said flexible sheet;
pulling said second end portion of said slide through said tunnel, allowing said raised portion of said slide to push against said bottom surface of the flexible sheet, causing said tissue to be pushed against the blades of said cover; and
disassembling said cover and base member and removing said tissue therefrom.

23. The method of claim 22 wherein said blades cut said tissue by shearing.

24. The method of claim 23 wherein said shearing is caused by said raised portion of said slide producing a wave in said tissue to sequentially push portions of said tissue into said blade as said slide is pulled through said tunnel.

25. An apparatus for cutting tissue into a predetermined shape, comprising:
a cover comprising a top member with a plurality of blades embedded into said top member;
a base member removably securable to said cover and having a base piece with a center length and a channel disposed along said center length, said base piece further comprising a flexible sheet secured to said base piece, said base piece and said flexible sheet forming a tunnel;
a slide slidably mounted in said base member and having first and second ends and a raised portion on said first end; and
a plurality of attachments removably securable to said cover and said base and provided to secure said cover and said base member together.

26. The apparatus of claim 25 wherein said blades are configured in said top member such that said blades form a shape identical to the shape into which the tissue will be cut.

* * * * *

UNITED STATES PATENT AND TRADEMARK OFFICE
CERTIFICATE OF CORRECTION

PATENT NO. : 5,425,741
DATED : January 20, 1995
INVENTOR(S) : Lemp et al.

It is certified that error appears in the above-identified patent and that said Letters Patent is hereby corrected as shown below:

Column 6, line 47 replace "inner stem" with --inner stent--.
Column 6, line 48 replace " outer stem" with -- outer stent--.

Signed and Sealed this

Fifteenth Day of September, 1998

Attest:

BRUCE LEHMAN

*Attesting Officer*  *Commissioner of Patents and Trademarks*